United States Patent [19]

Eibl et al.

[11] Patent Number: 5,733,885
[45] Date of Patent: *Mar. 31, 1998

[54] METHOD OF PRODUCING A VIRUS-SAFE BIOLOGICAL PREPARATION

[75] Inventors: Johann Eibl; Gabriela Hummel, both of Vienna; Gerda Redl, Rutzendorf; Thomas Seelich; Peter Turecek, both of Vienna; Günter Wöber, Oberwaltersdorf, all of Austria

[73] Assignee: Immuno Aktiengesellschaft, Vienna, Austria

[*] Notice: The term of this patent shall not extend beyond the expiration date of Pat. No. 5,410,022.

[21] Appl. No.: 678,594

[22] Filed: Jul. 15, 1996

Related U.S. Application Data

[63] Continuation of Ser. No. 165,906, Dec. 14, 1993, Pat. No. 5,639,730.

[30] Foreign Application Priority Data

Dec. 16, 1992 [AT] Austria ................................ 2500/92
Aug. 3, 1993 [AT] Austria ................................ 1547/93

[51] Int. Cl.⁶ .................... A61K 35/14; C07K 14/475; C12N 7/06; A61L 2/16
[52] U.S. Cl. .................. 514/21; 422/28; 422/30; 422/32; 435/236; 435/238; 514/8; 514/12; 530/364; 530/380; 530/390.1; 530/416; 530/427; 530/830
[58] Field of Search .................. 514/12, 21; 530/8, 530/380, 381, 383, 389, 830, 418, 427, 364, 363, 416; 435/236, 288; 422/28, 29, 30, 31, 32, 33, 34, 36

[56] References Cited

U.S. PATENT DOCUMENTS

| | | | |
|---|---|---|---|
| 4,297,344 | 10/1981 | Schwinn et al. | 530/381 |
| 4,379,085 | 4/1983 | Williams | 530/381 |
| 4,404,187 | 9/1983 | Schwinn et al. | 530/381 |
| 4,405,603 | 9/1983 | Schwinn et al. | 530/381 |
| 4,440,679 | 4/1984 | Fernandes et al. | 530/363 |
| 4,585,654 | 4/1986 | Landaburu | 530/395 |
| 4,673,733 | 6/1987 | Chandra et al. | 530/344 |
| 4,814,435 | 3/1989 | Schwartz et al. | 530/383 |
| 4,857,320 | 8/1989 | Wither | 424/94.63 |
| 4,923,815 | 5/1990 | Tanaka et al. | 435/183 |
| 5,118,794 | 6/1992 | Grangeorge et al. | 530/363 |
| 5,132,406 | 7/1992 | Uemora et al. | 530/390.1 |
| 5,143,838 | 9/1992 | Kraus et al. | 435/214 |
| 5,151,499 | 9/1992 | Kameyaura et al. | 530/381 |
| 5,371,195 | 12/1994 | Grangeorge et al. | 530/383 |
| 5,410,022 | 4/1995 | Eible et al. | 530/383 |
| 5,610,147 | 3/1997 | Seelich | 514/21 |
| 5,639,730 | 6/1997 | Eibl et al. | |

FOREIGN PATENT DOCUMENTS

| | | |
|---|---|---|
| 1 527 261 | of 0000 | European Pat. Off. |
| 0 015 055 | 9/1980 | European Pat. Off. |
| 0 035 204 | 9/1981 | European Pat. Off. |
| 0 052 827 | 6/1982 | European Pat. Off. |
| 0 053 338 | 6/1982 | European Pat. Off. |
| 0 077 870 | 5/1983 | European Pat. Off. |
| 0 094 611 | 11/1983 | European Pat. Off. |
| 0 099 445 | 2/1984 | European Pat. Off. |
| 0 117 064 | 8/1984 | European Pat. Off. |
| 0 124 506 | 11/1984 | European Pat. Off. |
| 0 142 059 | 5/1985 | European Pat. Off. |
| 0 144 709 | 6/1985 | European Pat. Off. |
| 0 173 242 | 3/1986 | European Pat. Off. |
| 0 177 836 | 4/1986 | European Pat. Off. |
| 0 196 761 | 10/1986 | European Pat. Off. |
| 0 292 003 | 11/1988 | European Pat. Off. |
| 0 341 103 | 11/1989 | European Pat. Off. |
| 0 343 275 | 11/1989 | European Pat. Off. |
| 0 378 208 | 7/1990 | European Pat. Off. |
| 0 439 156 | 7/1991 | European Pat. Off. |
| 0 519 901 | 12/1992 | European Pat. Off. |
| 0 528 701 | 2/1993 | European Pat. Off. |
| 0 534 812 | 3/1993 | European Pat. Off. |
| 0 541 507 | 5/1993 | European Pat. Off. |
| 2916711 | 11/1980 | Germany |
| 82/03871 | 11/1982 | WIPO |
| 83/04371 | 12/1983 | WIPO |
| 88/08710 | 11/1988 | WIPO |
| WO 90/15613 | 12/1990 | WIPO |

OTHER PUBLICATIONS

Hartert, H., "Thrombosis and Bleeding Disorders", Academic Press, New York pp. 70–76 (1971).

Seelich, T., "Fibrinogen, Fibrin and Fibrin Glue. Side Effects of Therapy with Clotting Factor Concentrates", FK. Schattauer Verlag, Stuttgart, New York pp. 199–208 (1980).

Suomela, H., "Preparation and Properties of a Therapeutic Factor IX Concentrate", Vox Sanguinis, Journal of Blood Transfusion, Immunohaemotology and Immunopathology, vol. 33 pp. 37–50 (1977).

Clemens, R., "Wie Virussicher Sind Blut und Plasmaderivate?", Z. Allg. Med. 65, pp. 429–433 (1989).

Rubinstein, D.B., M.D., "Inability of Solvent–Detergent (S–D) Treated Factor VIII Concentrate to Inactivate Parvoviruses . . . ", American Journal of Hematology 35:142 (1990).

Prince, A.M. "The Development of Virus–Free Labile Blood Derivatives", Eur. J. Epidemiol., pp. 103–118 (Jun., 1987).

Chemical Abstracts, vol. 111, No. 22, 201439j, Nov. 27, 1989.

Chemical Abstracts, vol. 114, No. 5, 39082a, Feb. 4, 1991.

Rozenberg, XII International Congress on Blood Transfusion Abstracts, Moscow, pp. 473–475 (Aug. 17–23, 1969).

Chemical Abstracts, Pharmaceuticals, vol. 84, No. 16, 111640n, Apr. 19, 1976.

(List continued on next page.)

Primary Examiner—Nancy Degen
Attorney, Agent, or Firm—Foley & Lardner

[57] ABSTRACT

In a method of producing a virus-safe biological preparation by heating while preserving a least 50% of its biologic activity, a biologially compatible tenside is added to the preparation before heating and heating is carried out in the presence of the same, whereupon the tenside, preferably, is eliminated.

10 Claims, No Drawings

OTHER PUBLICATIONS

Commission of the European Communities, "Ad Hoc Working Party on Biotechnology/Pharmacy" 111/8115/89–EN Final, pp. 1–15.

Mannucci, P.M. et al., "Low Risk of Viral Infection After Adminstration of Vapor–Heated Factor VIII Concentrate", *Transfusion*, vol. 32, pp. 134–138 (1992).

Müller, W., "New Ion Exchangers for the Chromatography of Biopolymers", *Journal of Chromatography*, 510, pp. 133nn–140 (1990).

Signa Catalog (1992) p. 1470.

METHOD OF PRODUCING A VIRUS-SAFE BIOLOGICAL PREPARATION

This application is a Continuation of U.S. application Ser. No. 08/165,906, filed Dec. 14, 1993, now U.S. Pat. No. 5,639,730.

This invention relates to a method of producing a virus-safe biological preparation by heating while preserving a least 50% of its biologic activity, as well as the use of the method for increasing the virus safety of a biological preparation.

By biological preparations, preparations of biological origin that may be obtained, for instance, from body liquids, such as blood, or from cell cultures, are understood. With products of this type, there is the banger of getting contaminated by infectious agents upon contact with potentially infectious material.

The risk of transmission of viruses by blood products is known. By blood products, products of human or animal blood or plasma are understood, which are intended for therapeutic, prophylactic or diagnostic application. Such products may contain enzymes, proenzymes including coagulation factors, enzyme inhibitors, immunoglobulins, albumin, plasminogen, fibrinogen, fibronectin or plasma.

There is available comprehensive literature dealing with the inactivation of infectious agents by heating of blood products. The various methods comprise:

heating of blood products in aqueous solutions in the presence of stabilizing agents, heating of blood products in the dry state, heating of blood products in the solid wet state.

In all of these inactivation methods, it is sought to eliminate the potential infectivity of the preparations, yet to largely maintain their biologic activity.

By heating the blood products, both membrane-enveloped and non-enveloped viruses are attacked. This constitutes an essential advantage over those methods which are based on the membrane-solubilizing effect only of tensides and, if desired, of organic solvents.

A method of treating biological and pharmaceutical products by treatment with amphiphils (tensides) at a temperature of between 4° C. and 37° C. is described in EP-0 050 061. This treatment aims at inactivating hepatitis-B viruses and non-A, non-B hepatitis viruses (enveloped).

Likewise, according to the method of EP-0 278 487, aqueous protein solutions are mixed with up to 2 g/100 ml of a non-ionic detergent and subsequently are incubated at a low temperature, for instance, at 4° C., until a virus-inactivating effect has been obtained.

However, this treatment with detergents has the disadvantage that it merely affects enveloped viruses: If a tenside is present at a concentration above the micell-forming concentration (CMC), lipid-containing membranes are solubilized and the virus is inactivated. By contrast, viruses that do not have lipid-containing membranes per se, such as, e.g., hepatitis-A virus, yet may be enclosed in lipid vesicles, are liberated by tenside treatment and hence are activated rather than inactivated (cf. Manucci PM et al. (1992), The Lancet 339, 819 "Outbreak of Hepatitis A among Italian Patients with Haemophilia").

According to EP-0 124 044, a surface active agent is added to a fibronectin-containing solution in an amount of from 0.01 to 0.5% by weight, together with a polyol and a chelating agent, the solution being heated at a temperature ranging between 50° and 70° C. The low amount of surfactant protects fibronectin from denaturation by shearing forces.

Likewise, detergents are added to blood plasma as solubilizers, together with virus-inactivating agents (glycyrrhizic triterpenoid compounds), the plasma being maintained at a temperature of up to 60° C. (U.S. Pat. No. 5,186,945). In order to obtain the desired surface-active effect, very small amounts of non-ionic detergents are used, for instance, concentrations ranging between 0.001 and 5% by weight. The advantage of using such small amounts of detergent resides in that the latter need not be eliminated.

Furthermore, it is described in EP-0 131 740 that a method of inactivating viruses in a solution containing organic solvents may be carried out at a temperature ranging between 0° and 70° C. In doing so, 0.001 to 10% by weight of detergents are employed as wetting agents. However, it is necessary to stabilize the labile proteins when heating the solution. Thus, not only the labile proteins, but also the virus components are stabilized.

The method described in EP-0 159 311 has proved to be successful as a heat treatment of blood products in the solid state. Therein, blood products are lyophilized, are adjusted to a content of water, methanol or ethanol of more than 5% by weight and less than 70% by weight, and are heated to temperatures ranging between 50° and 121° C. in closed containers. This method kills even resistant viruses, such as vaccinia virus. In this case, virus inactivation proceeds very slowly such that a very long heating time and a very high temperature have to be applied.

To enhance the effectiveness of that method, the method according to EP-0 324 729 has been proposed. Therein, blood products are heated in the solid wet state in the presence of organic compounds. The portion of water, to the major extent, remains physically bound to the blood product, while the organic compound is present in the atmosphere in gaseous form. Suitable organic compounds are ethanol, ethyl acetate, diethyl ether, chloroform and the like. After inactivation has been completed, the organic compounds must be separated from the blood products. The improved method causes the vaccinia virus to be inactivated already after few hours of heating at 60° C.

A method of inactivating viruses in a product adsorbed on a solid phase is described in EP-0 197 554. The adsorbed product is contacted with a virus-inactivating agent, whereupon the solid phase is separated and washed. Finally, the product is desorbed again. Among others, an amphiphilic substance is described as the virus-inactivating agent, which may be anionic, cationic, zwitterionic and non-ionic. However, treatment can be effected at a temperature of from 0° to 50° C. only.

It is the object of the invention to provide a method of producing a virus-safe preparation containing a labile protein by heating, whose efficiency is enhanced as compared to hitherto known heat treatments, the biologic activity of the preparation being substantially preserved.

Resistant viruses, such as vaccinia virus, are to be inactivated as rapidly and completely as possible in order not to unnecessarily reduce the biologic activity of the preparation.

In accordance with the invention, this object is achieved by a method of producing a virus-safe biological preparation by heating while preserving at least 50% of its biologic activity, which method is characterized in that a tenside is added to the preparation before heating and heating is carried out in the presence of said tenside, whereupon said tenside, preferably, is eliminated. It has been shown that the addition of a tenside to the preparation before the heat treatment will increase the effectiveness in a synergistic manner without substantially reducing the biologic activity of the preparation. After the heat treatment, the tenside is separated from the preparation.

Suitable tensides primarily are biologically compatible anionic, cationic, non-ionic or zwitterionic amphiphils. In general, tensides are considered as biologically compatible if at the concentration used they do not lyze erythrocytes in a standardized in vitro test (Cf. Pape et al., Arzneim.-Forsch./Drug. Res. 40, 498–502, 1990).

There may be used, for instance, tensides of the following groups:
- polyoxyethylene sorbitane esters (Tween® compounds),
- alkylphenolpolyethylene glycol ethers or their formaldehyde polymers (Triton® compounds),
- polyoxyethylene-polyoxypropylene block polymers (Pluronic® compounds),
- alkyl glycosides, such as, e.g., octyl-β-D glucoside,
- acid amide derivatives, such as, e.g., decanoyl-N-methyl glucamide (MEGA-10),
- anionic tensides, such as, e.g., sodium desoxycholate, cationic tensides, such as, e.g., benzyltrimethyl-ammonium chloride or benzyldimethyl-2-hy droxy ethyl-ammoniumchloride, and
- zwitterionic tensides, such as, e.g.,N-docecyl-N',N-dimethylammonio-3-propane sulfonate (sulfobetain SB12).

The tenside is added at a high concentration according to a tenside/protein ratio of at least 1:100, preferably of from 2:100 to 300:100, if the treatment of the preparation is carried out in its liquid or solid form. If the preparation has been adsorbed on a solid carrier and the heat treatment according to the invention is carried out on the solid carrier, treatment may be effected at even higher tenside concentrations of, for instance, up to 98% by weight.

Likewise, the invention comprises a method of increasing the virus safety of a biological preparation by preserving at least 50%, preferably 80%, of the biologic activity, in particular of the virus safety relative to enveloped and non-enveloped viruses, wherein the preparation is heated in the presence of a tenside at a concentration of at least 1% by weight, preferably more than 10% by weight, up to 98% by weight.

Although virus inactivation by means of tensides has been described in the prior art only as being effective against enveloped viruses, the desired effect also may be obtained in respect of non-membrane-enveloped viruses if the method according to the invention is carried out.

The present method is, of course, also suited to inactivate virus aggregates or vesicular structures harboring viruses, for instance, hepatitis-A viruses.

A substantial denaturation of proteins in the product heated according to the invention cannot be observed. Surprisingly, heat-labile proteins were even stabilized by the presence of tensides. The method according to the invention surprisingly is suitable for stabilizing a biological preparation mostly containing heat-labile proteins, during heat treatment. The preservation of the biologic activity during heat treatment is important primarily with such heat-labile proteins. Treatment of heat-stable preparations, for instance, of an albumin preparation, is less critical, though. Consequently, the invention primarily is related to a method of producing a preparation containing heat-labile proteins, except for an albumin preparation.

According to the invention, preparations can be produced in the first place, that contain labile plasmatic proteins, such as factors of coagulation, fibrinolysis and thrombolysis, or proenzymes and enzymes, or inhibitors thereof.

The heat treatment according to the invention, of the preparation in question preferably is carried out in the solid state, yet it also may take place in an aqueous solution or in suspension.

A preferred embodiment of the method according to the invention is carried out in that the tenside is added to the preparation in solution, whereupon the latter is lyophilized and is heated in the lyophilized state, the heating in this case being feasible at substantially higher temperatures. The heating advantageously is effected in the solid wet state, e.g., in the lyophilized preparation having a water content of more than 5% by weight and less than 70% by weight, in a closed container at a temperature ranging between 50° and 121° C. for at least 10 minutes, until the potential infectivity of the preparation has been eliminated, preferably 1 to 30 hours at 60° to 80° C.

It is also possible to heat an aqueous solution containing blood coagulation factor XIII in accordance with the invention without using conventional stabilizers.

Heat treatment in solution or suspension is carried out at a temperature of from 55° to 65° C., preferably at about 60° C., and for a period of time sufficient to inactivate possibly present viruses, preferably for 2 minutes to 100 hours. Most preferred is a treatment time of 30 minutes to 30 hours. The time required to carry out the method according to the invention can be determined in a preliminary assay by means of model viruses, such as, Human Immunodeficiency, Sindbis, polio, TBE and vaccinia viruses. A virus added prior to heating must not be detectable after heating.

The preparation obtained is characterized by a low portion of denaturation products, since despite heating at least 50%, preferably at least 80%, of the biologic activity of the preparation remains preserved. It could be observed that no turbidity occured in a solution of the preparation as usually does upon heating of highly concentrated preparations. The absorbance $E_{660}$ of the preparation heated according to the invention in a solution having a protein content of at least 5% by weight is less than 0.1 (at a light path of 1 cm, reference: water). As a result, an optically clear product in solution, largely free of denaturation substances is, thus, obtained.

It has been proved that the addition of a solubilizer prior to heating of a solution in accordance with the invention is advantageous. A factor XIII-containing solution may, for instance, be mixed with arginine in order to enhance the effect of the tenside action on the reduction of turbidity formation.

The addition of conventional stabilizers, such as, e.g., polyols and/or aminoacids or derivatives thereof, may be largely avoided. This has the advantage that virus inactivation proceeds more quickly and the effectiveness of the heat treatment is considerably enhanced. Besides, the elimination of conventional stabilizers is cumbersome and, thus, can be avoided.

Due to the excellent virucidal activity of the highly concentrated tensides, the use of organic solvents may be avoided. Therefore, the preparation treated in accordance with the invention does not contain any toxic traces of organic solvents.

A further embodiment of the method according to the invention comprises the addition of carbohydrates to the biological preparation, the hydration of proteins present, thus, being ensured even after lyophilization. Thus, it is possible to admix, e.g., sucrose or sorbitol in order to hydrate proteins in the preparation.

According to another aspect of the invention, the virus-inactivating heat treatment is performed at a preparation adsorbed on a solid carrier, the adsorbed preparation being suspended in a solution of a tenside during heating. After heating, the virus-inactivated preparation can be separated from the carrier in a known manner. Blood factors, such as factors of the prothrombin complex, are adsorbed, for instance, on an ion exchanger or on an affinity matrix and are suspended in an aqueous solution in the presence of high tenside concentrations and heated.

Preferably, the tenside may be separated from the preparation by suitable measures, such as dialysis, chromatographic purification methods (e.g., by ion exchange chromatography) or protein precipitation. The treated preparation may, for instance, be adsorbed on a solid carrier and washed free of tensides. Precipitation of the proteins to be prepared by means of precipitating agents, such as ethanol, ammonium-sulfate or polyethyleneglycol, liquid phase extraction or phase separation by the addition of specific substances, such as mixtures of salts and polyethyleneglycol or soluble dextran, as well as solid phase extraction of tenside on C18 material (reversed phase chromatography) are similarly suitable methods for separating from the preparation at least the major portion of tenside. By appropriate tenside-eliminating measures for removing the tenside, the tenside concentration in the preparation preferably is reduced to less than 0.1% by weight, most preferably less than 0.01% by weight.

The enhanced effect of a heat treatment due to the presence of tensides is surprising. From EP-0 345 246 it is known to add a tenside to a tissue adhesive lyophilisate merely to shorten its time of reconstitution. In doing so, very small concentrations of tensides that proved to be toxicologically safe are used. The tenside either is incorporated into the lyophilisate or is added to the lyophilisate to be dissolved. Thus, the tenside remains in the lyophilized preparation and is not separated, but rather added to the preparation. As a result, the solubility of the lyophilisate is considerably improved, measured by the reconstitution time. No enhanced virus-inactivating effect is observed.

The enhanced effect of a heat treatment can be demonstrated if very small amounts of tenside are used in an aqueous solution, which have no inactivating effect on viruses per se. Thus, a virus titer can be adjusted in the presence of tensides, but is eliminated only by way of heat treatment.

The synergistic effect of the method according to the invention becomes apparent by comparing the kinetics of virus inactivation by way of heat treatment with and without a content of tenside in the preparation. Model viruses, such as vaccinia virus, Sindbis virus or SIV (Simian immunodeficiency virus), are inactivated more quickly in the presence of inherently ineffective amounts of tensides during the heat treatment of blood products in the solid wet state than during the same heat treatment of the preparation without tenside content. Under appropriate conditions, model viruses added to the preparation will be killed already after 10 minutes, and certainly after one hour, of heat treatment according to the invention.

The synergistic effect of tensides during a heat treatment was not to be expected. In fact, the solubilizing effect of tensides on membrane proteins is largely independent of the temperature prevailing. In the technical field, there has been the opinion that a given concentration of a tenside is either virus-inactivating or not, irrespective of the temperature.

Even though a synergistic effect, depending on the method, can be observed only if a tenside concentration has no virus-inactivating activity per se (at a concentration of below CMC), of course this effect also occurs at elevated tenside concentrations.

The invention will be explained in more detail by way of the following examples:

EXAMPLE 1

Heat treatment of a factor VIII preparation in the presence of octyl-β-D-glucoside.

A factor VIII-containing preparation was produced according to AT-391 808.

2.7 ml of a solution of this factor VIII-containing preparation (30 mg protein/ml) were mixed with 0.3 ml of a vaccinia virus suspension and 0, 3 and 15 mg octyl glucoside were added to the solution (0, 0.1, 0.5% by weight). The ratio of tenside to protein was 4:100 and 19:100, respectively. The mixture was lyophilized, adjusted to a water content of 30% by weight, 20% by weight, 10% by weight and <1% by weight (dry), respectively, and heated at 60° C. for 10 hours. The virus titer was each determined after 0, 1, 3 and 10 hours. Likewise, the specific activity of factor VIII was determined before and after heat treatment. The results of virus inactivation as well as the residual activites after heat treatments are indicated in Table 1.

The tenside was eliminated by chromatographic purification of factor VIII using an anion exchanger.

EXAMPLE 2

Heat treatment of a factor VIII preparation in the presence of Triton® X-100.

2.7 ml of the factor VIII-containing solution of Example 1 were mixed with 0.3 ml of a vaccinia virus suspension, and 15 mg Triton® X-100 (0.5% by weight) were added to the solution. The ratio of tenside to protein was 19:100. The solution was lyophilized and a water content of 20% by weight was adjusted. After this, heat treatment was effected at 60° C. The virus titer was determined after 0, 1, 3 and 10 hours. Likewise, the specific activity of factor VIII was determined. Virus inactivation and residual activities are apparent from Table 2.

The tenside was eliminated by chromatographic purification of factor VIII using an anion exchanger.

EXAMPLE 3

Heat treatment of a plasminogen preparation in the presence of Zwittergent® 3-10

1.8 ml of a solution containing lys-plasminogen, produced according to the method of AT-390 801, was mixed with 0.2 ml of a vaccinia virus suspension and 10 mg Zwittergent® 3-10 (0.5% by weight) were added to the solution. The ratio of tenside to protein was 1:100. The mixture was lyophilized and adjusted to a water content of 15% by weight. After this, it was heated to 60° C. and the virus titer was determined after 0, 1, 3 and 10 hours of heat treatment. Likewise, the specific activity before and after heat treatment was determined. The results are indicated in Table 3.

The tenside was eliminated by dialysis.

EXAMPLE 4

Heat treatment of a prothrombin complex preparation in the presence of Tween 80

A prothrombin complex factor preparation was produced according to the method of Brummelhuis ("Methods of Plasma Protein Fractionation", J. M. Curling (ed.), p. 117 et seq., Acad. Press, 1980). 1.35 ml of a solution of this preparation was mixed with 0.15 ml of a Sindbis virus suspension and 75 mg Tween 80 were added to the solution (5% by weight). The ratio of tenside to protein was 5:100. The mixture was lyophilized and a water content of 9% by weight was adjusted. Heat treatments were effected at 60° C. and at 80° C. The virus titers were determined after 0, 1, 3 and 10 hours of heat treatment at 60° C. as well as after another hour of heat treatment at 80° C. and, in a separate run, after 20, 40 and 60 minutes at 80° C. The specific activity was determined before and after heat treatment, the results being indicated in Table 4.

The tenside was eliminated by chromatographic purification of the prothrombin complex using an anion exchanger.

EXAMPLE 5

Heat treatment of a fibrinogen preparation in the presence of MEGA-10.

Plasma was fractionated according to Cohn and a Cohn I fraction containing fibrinogen was produced. 1.8 ml of a solution of this fraction was mixed with 0.2 ml of a vaccinia virus suspension and decanoyl-N-methyl glucamide (MEGA-10) was added to the solution such that its concentration in the solution was 0.2% by weight. The ratio of tenside to protein was 2.5:100.The mixture was lyophilized and a water content of 10% by weight was adjusted. The lyophilisate was heated to 60° C. for 10 hours, subsequently to 80° C. for 3 hours and, in a separate run, to 80° C. for 3 hours. The virus titer was determined after 0, 1, 3 and 10 hours of heating (60° C.) as well as after another 3 hours (80° C.). Likewise, the virus titer was determined after 1, 2 and 3 hours of heating (80° C.). The specific activity of fibrinogen was determined as the clottable protein per volume unit before and after heat treatment. The results are indicated in Table 5.

The tenside was eliminated by precipitation of fibrinogen with glycine.

EXAMPLE 6

Heat treatment of a thrombin preparation in the presence of 0.5% octyl-β-D-glucoside.

A thrombin preparation was produced according to the method of Austrian Patent Application A 2183/91.

1.8 ml of a solution of this thrombin preparation was mixed with 0.2 ml of a SIV suspension and 10 mg octyl glucoside were added to the solution (0.5% by weight). The ratio of tenside to protein was 10:100. The mixture was lyophilized and a water content of 10% by weight was adjusted. Heat treatment was effected at a temperature of 60° C. The specific activity was determined before and after heat treatment. The virus titer was each determined after 0, 1, 3, 6 and 10 hours of heat treatment. The results are indicated in Table 6.

The tenside was eliminated by chromatographic purification of thrombin on an anion exchanger.

EXAMPLE 7

Heat treatment of a C1-esterase inhibitor preparation in the presence of 0.5% octyl-β-D-glucoside.

A C1-esterase inhibitor preparation was produced according to the method of Vogelaar et al. (1973) Vox Sang. 26, 118–127.

1.8 ml of a solution of this preparation was mixed with 0.2 ml of a vaccinia virus suspension and 10 mg octyl glucoside (0.5 by weight) were added to the solution. The ratio of tenside to protein was 12.5:100. The mixture was lyophilized, a water content of 15% by weight was adjusted and it was heated to 60° C. The virus titer was each determined after 0, 1, 3, 6 and 10 hours of heat treatment. The specific activity was determined before and after heat treatment. The results are indicated in Table 7.

The C1-esterase inhibitor was adsorbed on DEAE-Sephadex and washed free of tenside with a buffer.

The results of the assays represented in Tables 1 to 7 clearly demonstrate that substantially increased rates of inactivation of viruses are obtained when applying the method according to the invention as compared to heat treatments without tenside.

The different detection limits of the virus titers in the methods compared result from the choice of the detection method implied by the presence of tensides. Howe er, these different detection limits are of no relevance in this context.

TABLE 1

Inactivation of vaccinia virus in a factor VIII-containing preparation by heat treatment in the presence of octyl glucoside

| Time of heat treatment at 60° C. (h) | Water Content in Lyophilisate | | | | | | | | | | | | | | | |
|---|---|---|---|---|---|---|---|---|---|---|---|---|---|---|---|---|
| | 30% | | | | 20% | | | | 10% | | | | dry | | | |
| | 0 | 1 | 3 | 10 | 0 | 1 | 3 | 10 | 0 | 1 | 3 | 10 | 0 | 1 | 3 | 10 |
| 0.5% octylglucoside | | | | | | | | | | | | | | | | |
| Virus titer (ml$^{-1}$) | n.d.* | n.d. | n.d. | n.d. | $10^{4.4}$ | $\leq 10^{1.5}$ | $\leq 10^{1.5}$ | $\leq 10^{1.5}$ | $10^{6.4}$ | $10^{4.2}$ | $10^{3.7}$ | $\leq 10^{1.5}$ | $10^{6.9}$ | $10^{6.7}$ | $10^{6.6}$ | $10^{6.5}$ |
| Spec. activity (U/ml) | n.d. | n.d. | n.d. | n.d. | 24.5 | n.d. | n.d. | 14.9 | 25.8 | n.d. | n.d. | 20.6 | 31.5 | n.d. | n.d. | 28.5 |
| 0.1% octylglucoside | | | | | | | | | | | | | | | | |
| Virus titer | $10^{6.9}$ | $10^{4.6}$ | $\leq 10^{1.5}$ | $\leq 10^{1.5}$ | $10^{7.1}$ | $10^{4.6}$ | $10^{3.5}$ | $\leq 10^{1.5}$ | $10^{7.2}$ | $10^{6.4}$ | $10^{6.0}$ | $10^{6.2}$ | $10^{7.6}$ | $10^{7.2}$ | $10^{7.4}$ | $10^{7.5}$ |
| Spec. activity (U/ml) | 25.8 | n.d. | n.d. | 13.4 | 27.8 | n.d. | n.d. | 16.5 | 26.4 | n.d. | n.d. | 16.1 | 37.7 | n.d. | n.d. | 30.2 |
| No octylglucoside | | | | | | | | | | | | | | | | |
| Virus titer (ml$^{-1}$) | $10^{7.2}$ | $10^{6.6}$ | $10^{4.5}$ | $10^{4.5}$ | $10^{6.2}$ | $10^{7.5}$ | $10^{5.9}$ | $10^{5.7}$ | $10^{6.9}$ | $10^{6.7}$ | $10^{7.6}$ | $10^{7.0}$ | $10^{7.2}$ | $10^{7.0}$ | $10^{7.5}$ | $10^{7.1}$ |
| Spec. activity (U/ml) | 38 | n.d. | n.d. | 20.2 | 28.5 | n.d. | n.d. | 21.7 | 27.7 | n.d. | n.d. | 21.0 | 30.5 | n.d. | n.d. | 28.7 |

*n.d. . . . not determined

TABLE 2

Inactivation of vaccinia virus in a factor VIII-containing preparation by heat treatment in the presence of Triton$^R$ X-100

| Time of heat treatment at 60° C. (h) | 0 | 1 | 3 | 10 |
|---|---|---|---|---|
| 0.5% Triton$^R$ X-100 | | | | |
| Virus titer (ml$^{-1}$) | $10^{5.0}$ | $\leq 10^{3.5}$ | $\leq 10^{3.5}$ | $\leq 10^{3.5}$ |
| Spec. activity (U/ml) | 25.8 | n.d.* | n.d. | 22.9 |
| Without Triton$^R$ X-100 | | | | |
| Virus titer (ml$^{-1}$) | $10^{6.1}$ | $10^{6.0}$ | $10^{5.0}$ | $\leq 10^{1.5}$ |
| Spec. activity (U/ml) | 25.7 | n.d. | n.d. | 20.6 |

*n.d. . . . not determined

TABLE 3

Inactivation of vaccinia virus in a plasminogen preparation by heat treatment in the presence of Zwittergent$^R$ 3-10

| Time of heat treatment at 60° C. (h) | 0 | 1 | 3 | 10 |
|---|---|---|---|---|
| With Zwittergent | | | | |
| Virus titer (ml$^{-1}$) | $10^{3.4}$ | $\leq 10^{1.5}$ | $\leq 10^{1.5}$ | $\leq 10^{1.5}$ |
| Spec. activity (μmol ml$^{-1}$ min$^{-1}$) | 487 | n.d.* | n.d. | 287 |
| Without Zwittergent | | | | |
| Virus titer (ml$^{-1}$) | $10^{6.1}$ | $10^{5.9}$ | $10^{4.9}$ | $\leq 10^{1.5}$ |
| Spec. activity (μmol ml$^{-1}$ min$^{-1}$) | 460 | n.d. | n.d. | 410 |

*n.d. . . . not determined

TABLE 4

Inactivation of vaccinia virus in a prothrombin complex preparation by heat treatment in the presence of Tween 80

| Time of heat treatment | 60° C. | | | | 60 + 80° C. | 80° C. | | |
|---|---|---|---|---|---|---|---|---|
| | 0 h | 1 h | 3 h | 10 h | 10 + 1 h | 20 min | 40 min | 60 min |
| With Tween 80 | | | | | | | | |
| Virus titer (ml$^{-1}$) | $10^{3.4}$ | $\leq 10^{2.5}$ | $\leq 10^{2.5}$ | $\leq 10^{2.5}$ | $\leq 10^{2.5}$ | $\leq 10^{2.5}$ | $\leq 10^{2.5}$ | $\leq 10^{2.5}$ |
| Spec. activity (U F IX/ml) | 209 | n.d.* | n.d. | n.d. | 176 | n.d. | n.d. | n.d. |
| Without Tween 80 | | | | | | | | |
| Virus titer (ml$^{-1}$) | $10^{5.1}$ | $10^{3.7}$ | $\leq 10^{1.5}$ | $\leq 10^{1.5}$ | $\leq 10^{1.5}$ | $10^{1.7}$ | $\leq 10^{1.5}$ | $\leq 10^{1.5}$ |
| Spec. activity (U F IX/ml) | 204 | n.d. | n.d. | n.d. | 192.8 | n.d. | n.d. | n.d. |

*n.d. . . . not determined

TABLE 5

Inactivation of vaccinia virus in a fibrinogen preparation by heat treatment in the presence of MEGA-10

| Time of heat treatment (h) | 60° C. | | | | 60 + 80° C. | 80° C. | | |
|---|---|---|---|---|---|---|---|---|
| | 0 | 1 | 3 | 10 | 10 + 3 | 1 | 2 | 3 |
| With tenside | | | | | | | | |
| Virus titer (ml$^{-1}$) | $10^{6.4}$ | $10^{6.7}$ | $10^{6.4}$ | $10^{5.9}$ | $\leq 10^{1.5}$ | $10^{4.4}$ | $\leq 10^{1.5}$ | $\leq 10^{1.5}$ |
| Spec. activity (%) | 100 | n.d.* | n.d. | n.d. | 90 | n.d. | n.d. | n.d. |
| Without tenside | | | | | | | | |
| Virus titer (ml$^{-1}$) | $10^{5.9}$ | $10^{4.9}$ | $10^{5.0}$ | $10^{4.4}$ | $\leq 10^{0.5}$ | $10^{3.4}$ | $10^{2.1}$ | $\leq 10^{0.5}$ |
| Spec. activity (%) | 100 | n.d. | n.d. | n.d. | 100 | n.d. | n.d. | n.d. |

*n.d. . . . not determined

TABLE 6

Inactivation of SIV in a thrombin preparation by heat treatment in the presence of octyl-β-D-glucoside

| Time of heat treatment at 60° C. (h) | 0 | 1 | 3 | 6 | 10 |
|---|---|---|---|---|---|
| With tenside | | | | | |
| Virus titer (ml$^{-1}$) | $10^{2.2}$ | $10^{2.0}$ | $\leq 10^{1.5}$ | $\leq 10^{1.5}$ | $\leq 10^{1.5}$ |
| Spec. activity (μmol ml$^{-1}$ min$^{-1}$) | 1057 | n.d.* | n.d. | n.d. | 1063 |
| Without tenside | | | | | |
| Virus titer (ml$^{-1}$) | $10^{3.5}$ | $10^{1.5}$ | $10^{0.6}$ | $\leq 10^{0.6}$ | $\leq 10^{0.6}$ |
| Spec. activity (μmol ml$^{-1}$ min$^{-1}$) | 927 | n.d. | n.d. | n.d. | 1075 |

*n.d. . . . not determined

TABLE 7

Inactivation of vaccinia virus in a Cl-esterase inhibitor preparation by heat treatment in the presence of octyl-β-D-glucoside

| Time of heat treatment at 60° C. (h) | 0 | 1 | 3 | 6 | 10 |
|---|---|---|---|---|---|
| With tenside | | | | | |
| Virus titer (ml$^{-1}$) | $10^{3.0}$ | $\leq 10^{1.5}$ | $\leq 10^{1.5}$ | $\leq 10^{1.5}$ | $\leq 10^{1.5}$ |
| Spec. activity (U/ml) | 40 | n.d.* | n.d. | n.d. | 31 |
| Without tenside | | | | | |
| Virus titer (ml$^{-1}$) | $10^{6.4}$ | $10^{1.7}$ | $10^{0.6}$ | $10^{0.6}$ | $\leq 10^{0.5}$ |
| Spec. activity (U/ml) | 39 | n.d. | n.d. | n.d. | 35 |

*n.d. . . . not determined

EXAMPLE 8

Heat treatment of activated prothrombin complex (FEIBA) bound to an ion exchanger in the presence of Tween-80 (inactivation of vaccinia virus).

15 mg DEAE-Sephadex A-50 (Pharmacia) were incubated for 15 minutes at room temperature with 1 ml of a solution of 30 g/l NaCl in water for swelling. After this, the gel was separated from the swelling precipitate by centrifugation. Subsequently, there were five washings of the gel with 1 ml buffer each (9 g/l Na$_2$HPO$_4$·2H$_2$O, 7 g/l NaCl, pH 7.0) and two further washings with buffers (7 g/l Na$_3$citrate·2H$_2$O, 7 g/l NaCl), resuspension and centrifugation being carried out again.

30 ml fresh frozen human citrated plasma were thawed at 0° to +4° C. and the cryoprecipitate incurred was separated by centrifugation at +2° C. The resulting "cryosupernatant" was incubated with the washed DEAE-Sephadex, FEIBA being generated and adsorbed on the gel together with the factors of the prothrombin complex and inert protein. After this, the co-adsorbed inert protein was eliminated from the DEAE-gel by washing with a buffer (9 g/l Na$_2$HPO$_4$·2H$_2$O, 7 g/l NaCl).

The buffer-moist gel-protein complex then was suspended with 1 ml undiluted Tween-80 at 60° C. for 10 minutes, 0.1 ml of a vaccinia virus suspension having been added before. The virus titer was determined after 2, 4, 6, 8 and 10 minutes. The suspension of the gel-protein complex in Tween-80 then was diluted to 1:10 with a solution of 30 g/l NaCl in water. In doing so, the active substance was eluted from the gel. The tenside was removed from this solution in a known manner by adsorption with Extracti-Gel™D Detergent Removing Gel (Pierce). The solution was then dialyzed against distilled water, frozen and lyophilized. After reconstitution of the lyophilisate, the FEIB activity was determined according to AT-350726.

A likewisely produced FEIBA preparation mixed with virus, yet not treated with hot tenside as well as a preparation without tenside and heat treatment served as controls.

The results of the analysis are apparent from Table 8.

TABLE 8

Heat treatment of activated prothrombin complex (FEIBA) bound to ion exchanger in the presence of Tween-80 (vaccinia)

| | Treatment time (min.) | | | | | |
|---|---|---|---|---|---|---|
| | 2 | 4 | 6 | 8 | 10 | Eluate after lyophilization |
| With Tween 80 | | | | | | |
| Virus titer (ml$^{-1}$) | $\leq 10^{1.5}$ | $\leq 10^{1.5}$ | $\leq 10^{1.5}$ | $\leq 10^{1.5}$ | $\leq 10^{1.5}$ | n.d. |
| Activity (U/ml) | n.d. | n.d. | n.d. | n.d. | n.d. | 20 |
| Without Tween 80 | | | | | | |
| Virus titer (ml$^{-1}$) | $10^{4.0}$ | $10^{3.1}$ | $\leq 10^{1.5}$ | $\leq 10^{1.5}$ | $\leq 10^{1.5}$ | n.d. |
| Acitivity (U/ml) | n.d. | n.d. | n.d. | n.d. | n.d. | 5 |
| Without Tween 80 and heat treatment | | | | | | |
| Virus titer (ml$^{-1}$) | n.d. | n.d. | n.d. | n.d. | $10^{5.3}$ | n.d. |
| Activity (U/ml) | n.d. | n.d. | n.d. | n.d. | n.d. | 24 | n.d. . . . not determined

EXAMPLE 9
Heat treatment of activated prothrombin complex (FEIBA) bound to an ion exchanger in the presence of Tween-80 (inactivation of TBE viruses).

FEIBA was produced in a manner analogous to Example 8. Yet, 0.1 ml of a TBE virus suspension was added for treatment of the buffer-moist gel-protein complex with undiluted Tween-80. The virus titer was determined after 0.5, 1, 1.5, 2, 3, 4, 7 and 10 minutes. The FEIB activity in the eluate was determined as described in Example 8.

A likewisely produced FEIBA preparation mixed with virus, yet not treated with tenside, as well as a like preparation without Tween-80 and heat treatment again served as controls.

The results of the analysis are apparent from Table 9.

gel-protein complex was separated from the solution and each washed with buffer 1 (4 g/l $Na_3$citrate·$2H_2O$, 7 g/l NaCl, 9 g/l $Na_2HPO_4$·$2H_2O$, 500 IU heparin/l, pH 7.5) and subsequently with buffer 2 (4 g/l $Na_3$citrate·$2H_2O$/1.7 g/l NaCl, 500 IU heparin/l, pH 7.5).

The washed gel then was suspended with 1 ml Tween-80 at 60° C. for 10 minutes for virus inactivation. The tenside solution was mixed with 0.1 ml of a vaccinia virus suspension. The virus titer was determined after 2, 4, 6, 8 and 10 minutes. The suspension of the gel-protein complex in Tween-80 subsequently was diluted to 1:10 with a solution of 1 g/l $Na_3$citrate·$2H_2O$, 30 g/l NaCl, 1000 IU heparin/l, pH 7.9. In doing so, the prothrombin complex was eluted. The tenside was removed from this solution in a known manner by adsorption with Extracti-Gel™D Detergent Removing

TABLE 9

Heat treatment of activated prothrombin complex (FEIBA) bound on ion exchanger in the presence of Tween 80 (TBE)

| | Treatment time (min.) | | | | | | | | Eluate after lyophilization |
|---|---|---|---|---|---|---|---|---|---|
| | 0.5 | 1 | 1.5 | 2 | 3 | 4 | 7 | 10 | |
| With Tween 80 | | | | | | | | | |
| Virus titer ($ml^{-1}$) | $<10^0$ | $<10^0$ | $<10^0$ | $<10^0$ | $<10^0$ | n.d. | n.d. | n.d. | n.d. |
| Activity (U/ml) | n.d. | n.d. | n.d. | n.d. | n.d. | n.d. | n.d. | n.d. | 20 |
| Without Tween 80 | | | | | | | | | |
| Virus titer ($ml^{-1}$) | n.d. | $10^{3.6}$ | n.d. | $<10^0$ | n.d. | $<10^0$ | $<10^0$ | $<10^0$ | n.d. |
| Activity (U/ml) | n.d. | n.d. | n.d. | n.d. | n.d. | n.d. | n.d. | n.d. | 5 |
| Without Tween 80 and heat treatment | | | | | | | | | |
| Virus titer ($ml^{-1}$) | n.d. | n.d. | n.d. | n.d. | n.d. | n.d. | n.d. | $10^{6.2}$ | n.d. |
| Activity (U/ml) | n.d. | n.d. | n.d. | n.d. | n.d. | n.d. | n.d. | n.d. | 24 | n.d. ... not determined

EXAMPLE 10
Heat treatment of prothrombin complex bound to an ion exchanger in the presence of Tween-80 (inactivation of vaccinia viruses).

30 ml fresh frozen human citrated plasma were thawed at 0° to 4° C. and the cryoprecipitate incurred was separated by centrifugation at +2° C. The resulting "cryosupernatant" was mixed with 2 IU heparin/ml. After this, the solution of the proteins of the prothrombin complex were adsorbed with 0.5 mg DEAE-Sephadex A-50 (Pharmacia) per milliliter. The Gel (Pierce). The solution containing the prothrombin complex was rebuffered against a buffer containing 4 g/l $Na_3$citrate·$2H_2O$ and 8 g/l NaCl, pH 7.0 and lyophilized.

The protein content as well as coagulation factors II, VII, IX and X were determined in the reconstituted prothrombin complex.

A prothrombin complex produced as described above, yet without tenside treatment, and a preparation without tenside and heat treatment served as controls.

The results are apparent from Table 10.

TABLE 10

Heat treatment of prothrombin complex bound to ion exchanger in the presence of Tween-80 (vaccinia)

| | Treatment time (min.) | | | | | Eluate after lyophilization Factor | | | |
|---|---|---|---|---|---|---|---|---|---|
| | 2 | 4 | 6 | 8 | 10 | II | VII | IX | X |
| With Tween 80 | | | | | | | | | |
| Virus titer ($ml^{-1}$) | $\leq 10^{1.5}$ | $\leq 10^{1.5}$ | $\leq 10^{1.5}$ | $\leq 10^{1.5}$ | $\leq 10^{1.5}$ | ... | n.d. | ... | ... |
| Spec. activity (U/mg protein) | n.d. | n.d. | n.d. | n.d. | n.d. | 1.8 | 0.3 | 1.3 | 1.4 |
| Without Tween 80 | | | | | | | | | |
| Virus titer ($ml^{-1}$) | $10^{4.0}$ | $10^{3.1}$ | $\leq 10^{1.5}$ | $\leq 10^{1.5}$ | $\leq 10^{1.5}$ | ... | n.d. | ... | ... |
| Spec. activity (U/mg protein) | n.d. | n.d. | n.d. | n.d. | n.d. | 1.9 | 0.3 | 0.7 | 0.6 |

TABLE 10-continued

Heat treatment of prothrombin complex bound to ion exchanger in the presence of Tween-80 (vaccinia)

| | Treatment time (min.) | | | | | Eluate after lyophilization Factor | | | |
|---|---|---|---|---|---|---|---|---|---|
| | 2 | 4 | 6 | 8 | 10 | II | VII | IX | X |
| Without Tween 80 and heat treatment | | | | | | | | | |
| Virus titer (ml⁻¹) | n.d. | n.d. | n.d. | n.d. | $10^{5.3}$ | ... | n.d. | ... | ... |
| Spec. activity (U/mg protein) | n.d. | n.d. | n.d. | n.d. | n.d. | 1.9 | 0.3 | 2.1 | 1.5 | n.d. ... not determined

EXAMPLE 11

Heat treatment of prothrombin complex bound to ion exchanger in the presence of Tween-80 (inactivation of TBE viruses).

Prothrombin complex was produced in a manner analogous to Example 10. Yet, 0.1 ml of a TBE virus suspension was added for treatment of the buffer-moist gel protein complex with undiluted Tween-80. The virus titer was determined after 0.5, 1, 1.5, 2, 3, 4, 7 and 10 minutes. The protein content as well as coagulation factors II, VII, IX and X were determined in the reconstituted prothrombin complex.

A prothrombin complex produced as described above, yet without tenside treatment, and a preparation without tenside and heat treatment served as controls.

The results are apparent from Table 11.

The precipitate was dissolved in a citrated buffer solution, pH 7.0 (5.4 g/l $Na_3$citrate·$2H_2O$, 7 g/l NaCl, 100 KIU aprotinin/l) and heated to 56° C. for 10 minutes. The precipitate formed of denaturated fibrinogen was centrifuged off. The heat precipitation supernatant was freed of accompanying proteins by precipitation with 3.5% by weight of PEG 4000 at 4° C. Subsequently, factor XIII was precipitated by the addition of PEG 4000 up to a concentration of 10% by weight at 4° C., separated by centrifugation and dissolved in 1/25 of the original volume of an 0.1% by weight sodium citrate buffer (pH 7.0).

The specific activity was 21 U factor XIII/mg protein. The solution was divided, one portion being mixed with 1% by

TABLE 11

Heat treatment of activated prothrombin complex bound to ion exchanger in the presence of Tween-80 (TBE)

| | Treatment time (min) | | | | | | | | Eluate after lyophilization Factor | | | |
|---|---|---|---|---|---|---|---|---|---|---|---|---|
| | 0.5 | 1 | 1.5 | 2 | 3 | 4 | 7 | 10 | II | VII | IX | X |
| With Tween 80 | | | | | | | | | | | | |
| Virus titer (ml⁻¹) | <10⁰ | <10⁰ | <10⁰ | <10⁰ | <10⁰ | n.d. | n.d. | n.d. | ... | n.d. | ... | ... |
| Spec. activity (U/mg protein) | n.d. | n.d. | n.d. | n.d. | n.d. | n.d. | n.d. | n.d. | 1.8 | 0.3 | 1.3 | 1.4 |
| Without Tween 80 | | | | | | | | | | | | |
| Virus titer (ml⁻¹) | n.d. | $10^{3.6}$ | n.d. | <10⁰ | n.d. | <10⁰ | <10⁰ | <10⁰ | ... | n.d. | ... | ... |
| Spec. activity (U/mg protein) | n.d. | n.d. | n.d. | n.d. | n.d. | n.d. | n.d. | n.d. | 1.9 | 0.3 | 0.7 | 0.6 |
| Without Tween 80 and heat treatment | | | | | | | | | | | | |
| Virus titer (ml⁻¹) | n.d. | n.d. | n.d. | n.d. | n.d. | n.d. | n.d. | $10^{6.2}$ | ... | n.d. | ... | ... |
| Spec. activity (U/mg protein) | n.d. | n.d. | n.d. | n.d. | n.d. | n.d. | n.d. | n.d. | 1.9 | 0.3 | 2.1 | 1.5 | n.d. ... not determined

EXAMPLE 12

Stability of factor XIII when heated in a solution (without stabilizers) in the presence of a tenside.

A plasma fraction (Cohn I precipitate) was dissolved with 10 times the amount of a citrated buffer solution, pH 7.0 (13.4 g/l $Na_3$citrate·$2H_2O$, 29 g/l NaCl, 20000 KIU aprotinin/l). After addition of ammonium sulfate to 16% saturation (at room temperature) it was cooled to 4° C. and the mixture was stirred for another 2 hours. The precipitate formed was dissolved with the buffer solution and precipitation with ammonium sulfate was repeated once.

weight of Tween 80. Both solutions were heated to 60° C. for 6 hours. The factor XIII residual activities after 6 hours of heating were 82% without tenside added and 84% with tenside added.

EXAMPLE 13

Example 12 was repeated with various tensides in different concentrations (heating: 4 hours, 60° C.).

TABLE 12

Heating of a factor XIII-containing solution in the presence of tenside

| Tenside | Concentration % by weight | FXIII Residual Activity % |
|---|---|---|
| Tween 80 | 15 | 97 |
| Triton X-100 | 15 | 91 |
| Pluronic P 85 | 10 | 96 |

Examples 12 and 13 demonstrate that heat treatment of factor XIII in the presence of tensides is feasible without having to take into account major losses of factor XIII activity.

Example 14 below illustrates the surprisingly enhanced inactivation kinetics of a model virus by a heat treatment in the presence of a tenside as compared to a heat treatment without tenside addition.

EXAMPLE 14

Inactivation of a model virus (Sindbis) in a factor XIII-containing solution in the presence or absence of a tenside.

A factor XIII-containing solution corresponding to Example 12 was divided, one portion being mixed with 0.3% by weight of n-octyl glucoside.

Both solutions were heated to 60° C., mixed with 10% by vol. of a Sindbis virus suspension (starting of the virus inactivation reaction) and further incubated at 60° C. Samples were taken at given time intervals and the virus titer was determined.

The results are summarized in Table 13 below.

TABLE 13

Virus inactivation in factor XIII-containing solution with and without tenside at 60° C.

| Time of heating at 60° C. (minutes) | without tenside | with tenside |
|---|---|---|
| 0 | 8.1 | 8.1 |
| 0.5 | 5.75 | 1.88 |
| 1 | 5.0 | ≦1.5 |
| 1.5 | 4.25 | ≦1.5 |
| 2 | 3.88 | ≦1.5 |
| 2.5 | 3.75 | ≦1.5 |
| 3 | 3.25 | ≦1.5 |
| 3.5 | 2.75 | ≦1.5 |
| 4 | 2.63 | ≦1.5 |
| 4.5 | 2.5 | ≦1.5 |
| 5 | 2.38 | ≦1.5 |
| 6 | 1.88 | ≦1.5 |
| 7 | 2.1 | ≦1.5 |
| 8,10,15,20,30 | ≦1.5 | ≦1.5 |

By the addition of tenside, an even more rapid and comprehensive virus inactivation is obtained without having to take into account major losses of factor XIII activity (cf. Example 13).

What we claim is:

1. A virus-safe biologial preparation produced by using a tenside and by heating said preparation in the presence of said tenside while preserving at least 50% of its biological activity, which virus-safe biological preparation is optically clear in solution.

2. A virus-safe biological product that is essentially free of denaturation products, wherein said virus-safe biological product is obtainable by heating a biological preparation having a level of biological activity, wherein said virus-safe biological product has a level of activity that is at least 50% of the level prior to heating and contains a tenside in an aqueous solution.

3. A virus-safe biological product according to claim 1, wherein said virus-safe biological product is substantially free of toxic organic solvents.

4. A virus-safe biological product according to claim 1, wherein said virus-safe biological product is a stable pharmaceutical product.

5. A virus-safe biological product according to claim 1, wherein said virus-safe biological product is optically clear when in solution.

6. A virus-safe biological product according to claim 1, wherein said virus-safe biological product comprises a blood protein.

7. A virus-safe biological product according to claim 6, wherein said blood protein is factor VIII, factor XIII, fibronectin, thrombin, fibrinogen or plasminogen.

8. A virus-safe biological product according to claim 1, wherein said virus-safe biological product comprises an enzyme, a proenzyme, an inhibitor, an immunoglobulin or albumin.

9. A virus-safe biological product according to claim 8, wherein said wherein said virus-safe biological product comprises C1-esterase inhibitor.

10. A virus-safe biological product according to claim 1, wherein said virus-safe biological product is a prothrombin complex or an activated prothrombin complex.

* * * * *